US009184099B2

(12) United States Patent
Baghbani-Parizi et al.

(10) Patent No.: US 9,184,099 B2
(45) Date of Patent: Nov. 10, 2015

(54) BIOSENSOR DEVICES, SYSTEMS AND METHODS THEREFOR

(75) Inventors: Kosar Baghbani-Parizi, Los Altos, CA (US); Yoshio Nishi, Los Altos, CA (US); Hesaam Esfandyarpour, Los Altos, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 36 days.

(21) Appl. No.: 13/252,315

(22) Filed: Oct. 4, 2011

(65) Prior Publication Data
US 2012/0138460 A1    Jun. 7, 2012

Related U.S. Application Data

(60) Provisional application No. 61/389,590, filed on Oct. 4, 2010.

(51) Int. Cl.
| | |
|---|---|
| G01N 27/414 | (2006.01) |
| H01L 21/02 | (2006.01) |
| H01L 29/66 | (2006.01) |
| H01L 21/84 | (2006.01) |
| B82Y 15/00 | (2011.01) |
| H01L 27/12 | (2006.01) |
| B01L 3/00 | (2006.01) |

(52) U.S. Cl.
CPC ............ *H01L 21/84* (2013.01); *B82Y 15/00* (2013.01); *G01N 27/4145* (2013.01); *H01L 27/1203* (2013.01); *B01L 3/502753* (2013.01)

(58) Field of Classification Search
USPC ............ 204/409, 452, 603; 438/49; 257/253, 257/414
See application file for complete search history.

(56) References Cited

U.S. PATENT DOCUMENTS

| 5,466,348 A | 11/1995 | Holm-Kennedy |
| 6,870,235 B2 | 3/2005 | Abstreiter et al. |

(Continued)

FOREIGN PATENT DOCUMENTS

WO    WO 2008/132643 A1 * 11/2008 ............. G01N 15/12

OTHER PUBLICATIONS

Parizi et al., SOI Conference, 2009 IEEE International, Oct. 5-8, 2009.*

(Continued)

*Primary Examiner* — Luan Van
*Assistant Examiner* — Steven Rosenwald
(74) *Attorney, Agent, or Firm* — Crawford Maunu PLLC

(57) ABSTRACT

A sensing apparatus for sensing target materials including biological or chemical molecules in a fluid. One such apparatus includes a semiconductor-on-insulator (SOI) structure having an electrically-insulating layer, a fluidic channel supported by the SOI structure and configured and arranged to receive and pass a fluid including the target materials, and a semiconductor device including at least three electrically-contiguous semiconductor regions doped to exhibit a common polarity. The semiconductor regions include a sandwiched region sandwiched between two of the other semiconductor regions, and configured and arranged adjacent to the fluidic channel with a surface directed toward the fluidic channel for coupling to the target materials in the fluidic channel, and further arranged for responding to a bias voltage. The sensing apparatus also includes an amplification circuit in or on the SOI and that is arranged to facilitate sensing of the target material near the fluidic channel.

19 Claims, 7 Drawing Sheets

(56) References Cited

U.S. PATENT DOCUMENTS

| | | | |
|---|---|---|---|
| 7,317,216 B2 | 1/2008 | Holm-Kennedy | |
| 2005/0098434 A1* | 5/2005 | Gundel et al. | 204/403.02 |
| 2005/0218464 A1* | 10/2005 | Holm-Kennedy | 257/414 |

OTHER PUBLICATIONS

Bobrow, Fundamentals of Electrical Engineering, 1985, Holt, Rinehart, and Winston, Inc.*

Moser et al., Biosens. & Bioelect. 17 (2002) 297-302.*

Parizi et al., SOI Conference, 2008. SOI. IEEE International, Oct. 6-9, 2008.*

Wilke et al (Biosens. and Bioelect. 19, 2003, 149-153).*

Kuhr, Anal. Chem. 1990, 62, 403R-414R.*

Hsu et al. "Wafer-scale silicon nanopillars and nanocones by Langmuir-Blodgett assembly and etching." Applied Physics Lett. 93, p. 133109-1-133109-3 (Oct. 2008).

Fritz et al. "Electronic detection of DNA by its intrinsic molecular charge." PNAS 99(22), p. 14142-14146 (Oct. 29, 2002).

Patolsky, Lieber et al. "Electrical detection of a single virus." PNAS 101(39), p. 14017-14022 (Sep. 28, 2004).

Cui et al. "Nanowire nanosensors for highly sensitive and selective detection of biological and chemical species." Science 293, p. 1289-1292 (Aug. 17, 2001).

Esfandyarpour. "Nano-Biotechnology toward Diagnostic Industry: Obstacles and Opportunities." NSTI-Nanotech, vol. 4, p. 421 (2007). Abstract Only.

Poghossian et al. "Possibilities and limitations of label-free detection of DNA hybridization with field-effect-based devices." Sensors and Actuators B 111-112, p. 470-480 (2005).

Pascault. "A Finite Element Study of the DNA Hybridization Kinetics on the Surface of Microfluidic Devices." Thesis, M.S. Chem. Engineer., Worcester Polytechnic Institute, p. 1-148 (Apr. 2007).

Ramos et al. "AC electric-field-induced fluid flow in microelectrodes." J Colloid Interface Sci 217, p. 420-422 (1999).

Brown et al. "AC electroosmotic flow in a DNA concentrator." Microfluid Nanofluid 2, p. 513-523 (May 2006).

Shen et al. "DNA Diffusion in Mucus: Effect of Size, Topology of DNAs, and Transfection Reagents." Biophysical Journal 91(2), p. 639-644 (Apr. 21, 2006).

Stein et al. Electrokinetic Concentration of DNA Polymers in Nanofluidic Channels, Nano Lett. 10, p. 765-772 (Feb. 2010).

Cheng et al. "Single-stranded DNA concentration by electrokinetic forces." J. Micro/Nanolith. MEMS MOEMS 8(2) 021107 (Jun. 9, 2009). Abstract only.

K. F. Lei et al. "Electrokinetic DNA concentration in Microsystems." Sensors and Actuators A 156(2) (Dec. 2009). Abstract only.

Williams et al. "Etch Rates for Micromachining Processing." J. Microelectromechanical Systems, vol. 5, No. 4, p. 761-778 (Dec. 1996).

K. B. Parizi et al. "An Internally Amplified Signal SOI Nano-bridge Biosensors for Electrical Detection of DNA Hybridization." IEEE Int'l SOI Conference, 2 pgs. (Oct. 5-8, 2009). Filed as part of APPENDIX B in the underlying provisional patent application.

K. B. Parizi et al. "Poster—An Internally Amplified Signal SOI Nanobridge Biosensor for Electrical Detection of DNA Hybridization or Sequence." Poster—1 sheet (Summer 2009). Filed as part of APPENDIX F in the underlying provisional patent application.

K. B. Parizi et al. "BioFET Sensor." CIS ADCOM Fall 2009—Stanford University, 28 pgs (Nov. 2009). Filed as part of Appendix D in the underlying provisional patent application.

K. B. Parizi et al. "A Semiconductor Nanobridge Biosensor for Electrical Detection of DNA Hybridization." IEEE Int'l SOI Conference, 2 pgs. (Oct. 6-9, 2008). Filed as part of APPENDIX A in the underlying provisional patent application.

K. B. Parizi. "BioFET for Detection of Biological Species." Stanford University, CIS (Computer-Information-System) Catalog, 1 sheet (2008). Filed as part of Appendix G in the underlying provisional patent application.

K. B. Parizi et al. "BioFET Sensor." CIS 2007—Stanford University, 33 pgs. (2007). Filed as part of APPENDIX H in the underlying provisional patent application.

K. B. Parizi et al. "Poster—BioFET Sensor." CIS 2007—Stanford University, 18 pgs. (2007). Filed as part of APPENDIX H in the underlying provisional patent application. Filed as part of Appendix E in the underlying provisional patent application.

\* cited by examiner

BIOSENSOR DEVICES, SYSTEMS AND METHODS THEREFOR

RELATED DOCUMENTS

This patent document claims benefit under 35 U.S.C. §119 to U.S. Provisional Patent Application Ser. No. 61/389,590, entitled "Biosensor Devices, Systems and Methods Therefor" and filed on Oct. 4, 2010; this patent document and the Appendices filed in the underlying provisional application, including the references cited therein, are fully incorporated herein by reference.

BACKGROUND

Despite technical improvements, bio-based and related sensor technology involving industries, such as the semiconductor industry, has been challenging to implement and/or use to obtain desirable results. For example, sensors used in biomedicine (biosensors) can be classified into categories including optical and electrical-based biosensors. Optical biosensors generally exhibit higher sensitivity and wider range of detection, but can suffer from lack of real time and label free detection. Electrical biosensors, such as impedance biosensors, can address issues relating to optical biosensors for applications such as point-of-care and disease discovery, using real time, low cost, ease of miniaturization and label-free operation. However, such electrical biosensors have also been challenging to implement.

These and other matters have presented and continue to present challenges to a variety of sensor technologies, including those relating to biomedical applications.

SUMMARY

Aspects of the present disclosure relate generally to biosensors, biosensor devices, biosensor systems and methods relating to their operation as discussed above.

One aspect of the present disclosure relates to a method, device and/or system directed to sensing a biological material using a sensor having a semiconducting channel bridge with one or more surfaces exposed for interacting with the biological material, and which may have a local amplifier.

Certain other, more specific, aspects of the disclosure are directed to a sensing apparatus for sensing target materials including biological or chemical molecules in a fluid. One such apparatus includes a substrate such as a semiconductor-on-insulator (SOI) structure including an electrically-insulating layer, a fluidic channel supported by the substrate structure and configured to receive and pass a fluid including the target materials, and a semiconductor device including at least three electrically-contiguous semiconductor regions doped to exhibit a common polarity. The semiconductor regions including a sandwiched region sandwiched between two of the other semiconductor regions, and configured and arranged adjacent to the fluidic channel with a surface directed toward the fluidic channel for coupling to the target materials in the fluidic channel, and further arranged for responding to a bias voltage. By doping two of the other semiconductor regions at a higher concentration than the sandwiched region, optionally with a bias voltage applied to a reference electrode or back bias source, and in response to the target materials in the fluidic channel, the three contiguous semiconductor regions facilitate an interaction to sense the presence of the target materials in the fluidic channel by passing current in a conducting mode from one of the end electrodes to the other of the end electrodes. Also, an amplification circuit in or on the SOI is arranged to facilitate sensing the target material near the fluidic channel.

Other aspects are directed to a method, device and/or system directed to sensing biological materials using a fluidic channel to receive and pass a fluid including the biological materials. A semiconductor channel bridging the microfluidic channel and having opposing surfaces exposed for coupling to biological materials in the microfluidic channel. Biological materials may change the surface potential of the semiconductor via a first surface of the semiconductor channel, and biological materials may apply a bias to the semiconductor channel via a second surface of the semiconductor channel that is opposite the first surface, with source and drain electrodes being connected by the semiconductor channel. An integrated amplifier amplifies current passing between the electrodes via the sandwiched semiconductor regions and biomolecules coupled or associated thereto, the current being indicative of a conductance characteristic of the channel as coupled to biological materials.

The above overview is not intended to describe each illustrated embodiment or every implementation of the present disclosure.

DESCRIPTION OF THE DRAWINGS AND EXAMPLE EMBODIMENTS

Various example embodiments may be more completely understood in consideration of the following detailed description in connection with the accompanying drawings, in which.

Figure 1A:
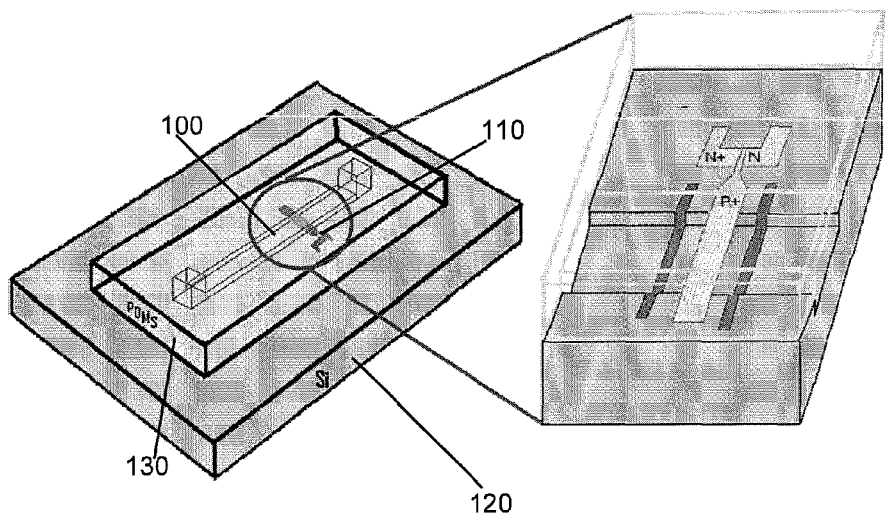
FIG. 1A shows an example embodiment of an apparatus for sensing biological materials including a microfluidic channel.

While the disclosure is amenable to various modifications and alternative forms, examples thereof have been shown by way of example in the drawings and will be described in detail. It should be understood, however, that the intention is not to limit the disclosure to the particular embodiments shown and/or described. On the contrary, the intention is to cover all modifications, equivalents, and alternatives falling within the spirit and scope of the disclosure.

DETAILED DESCRIPTION

Various aspects of the present disclosure are directed to sensors, including biosensors implementing impedance modulation with a nanobridge type of biosensor, for characterizing biochemical species such as antibodies and antigens, and/or for applications involving one or more of DNA sequencing, DNA hybridization, Real time PCR, protein or other bio-species and chemical-species detection. While the present disclosure may not be so limited, applications thereof may be appreciated using a discussion of example embodiments in this context.

In an example embodiment of the instant disclosure, an apparatus is configured and arranged to sense target materials. The target typically includes biological or chemical molecules in a fluid. The device may include a semiconductor-on-insulator (SOI) structure and an electrically-insulating layer. Alternately, the device may be fabricated on a silicon substrate without an insulating layer below the three electrically-contiguous semiconductor regions. In some embodiments the silicon substrate may be of opposite polarity of the three electrically-contiguous semiconductor regions. In some embodiments, a buried channel may be used to create a thin area of low conductivity zone for one or more of the electrically-contiguous semiconductor regions. A fluidic channel passes and receives the fluid, including the target materials, and may be located on and supported by the SOI structure. The apparatus further includes a semiconductor device which has at least three electrically-contiguous semiconductor regions. The at least three electrically-contiguous semiconductor regions are doped to exhibit a common polarity. In certain more specific embodiments, the common polarity is of a p-type doping scheme, and in other embodiments, the common polarity is an n-type doping scheme. In another embodiment, the different regions may have different doping polarities.

The semiconductor regions are characterized as having a region sandwiched between two of the other semiconductor regions. The sandwiched region is adjacent to the fluidic channel, and has a surface directed toward the fluidic channel for coupling to the target materials that pass through the channel. In certain specific embodiments, the surface includes beads which may be in the fluidic channel for target material attachment. The sandwiched region is further arranged to respond to a bias voltage.

In some embodiments, the surface directed towards the fluidic channel may be in direct contact with said channel. In other embodiments, the surface directed towards the fluidic channel may have a dielectric coating completely covering the surface of the sandwiched region which would otherwise be in direct contact with said fluidic channel. In other embodiments, the surface directed towards the fluidic channel may have a metal coating completely covering the surface of the sandwiched region which would otherwise be in direct contact with said fluidic channel. In yet other embodiments, a metal layer and a dielectric layer may completely cover the surface of the sandwiched region which would otherwise be in direct contact with said fluidic channel.

The two of the other semiconductor regions, the regions accomplishing the sandwiching of the aforementioned sandwiched region, are located at least partially on the electrically-insulating layer. The two of the other semiconductor regions are doped at a higher concentration than the sandwiched region, and are electrically connected to the end electrodes. In response to the change in surface potential due to the target materials in the fluidic channel, the at least three contiguous semiconductor regions facilitate an interaction, largely using the sandwiched region proximate fluid in the fluidic channel, to sense the presence of the target materials in the fluidic channel by passing current in a conducting mode from one of the end electrodes to the other of the end electrodes. The passing current is indicative of the conductance characteristic of the sandwiched semiconductor region, wherein said conductance may change in response to the presence of said target materials. In certain specific embodiments, the conducting mode is a depletion mode. In other embodiments, the conducting mode is an accumulation mode. The change in conductance in response to the target materials may be an increase or a decrease in the conductance of the sandwiched semiconductor region.

The apparatus further may include an amplification circuit, which may be supported by the SOI structure or the substrate semiconductor, and that is designed to facilitate sensing the target material near the fluidic channel by way of a change in the electric field.

In certain embodiments, the apparatus also includes an alternative set of at least three contiguous semiconductor regions. The alternative set is electrically isolated from the aforementioned first set by a layer of dielectric, and has a different doping specificity (e.g., higher or lower as compared to the first set of contiguous semiconductor regions). The alternative set may be arranged to operate in place of the first mentioned at least three contiguous semiconductor regions, or may be in addition to all three of the three contiguous semiconductor regions. In certain embodiments, the surface of the sandwiched semiconductor region, or the surface of another layer which may cover or overlay the sandwiched semiconductor region, may be exposed toward the fluidic channel, and may be textured to increase sensitivity.

The apparatus of the instant disclosure can be utilized in a number of ways. In an example embodiment, a fluid having target materials is provided through the fluidic channel. An electric field is applied in and around the channel, which facilitates sensitivity by inducing movement of molecules in the fluid. In certain specific embodiments, the electric field utilizes electrophoresis in application. In other embodiments, the electric field utilizes electro-osmosis. In addition to applying an electric field, a bias voltage may be applied to the sandwiched region by a reference electrode or back bias source, and the presence of the target materials is sensed by detecting a change in the current passed in a conducting mode in response to the voltage induced by the target materials, which may be further enhanced by an applied bias voltage. In an example embodiment, the method of utilizing the apparatus includes transitioning from a low-conducting mode to the high-conducting mode in sensing the presence of target molecules or vice versa.

In an example method of manufacturing an apparatus discussed herein, the SOI device is formed over (e.g., on or in a portion of) the insulating layer. In certain embodiments, the insulating layer is a buried-oxide layer. Further, the at least three semiconductor regions are doped to the common polarity desired. In certain embodiments, a set of at least three alternative contiguous semiconductor regions are formed on the insulating layer. The alternative set has a different doping specificity as compared to the first set of at least three semiconductor regions, and can operate in place of the first mentioned of the at least three contiguous semiconductor regions.

Figure 1B:
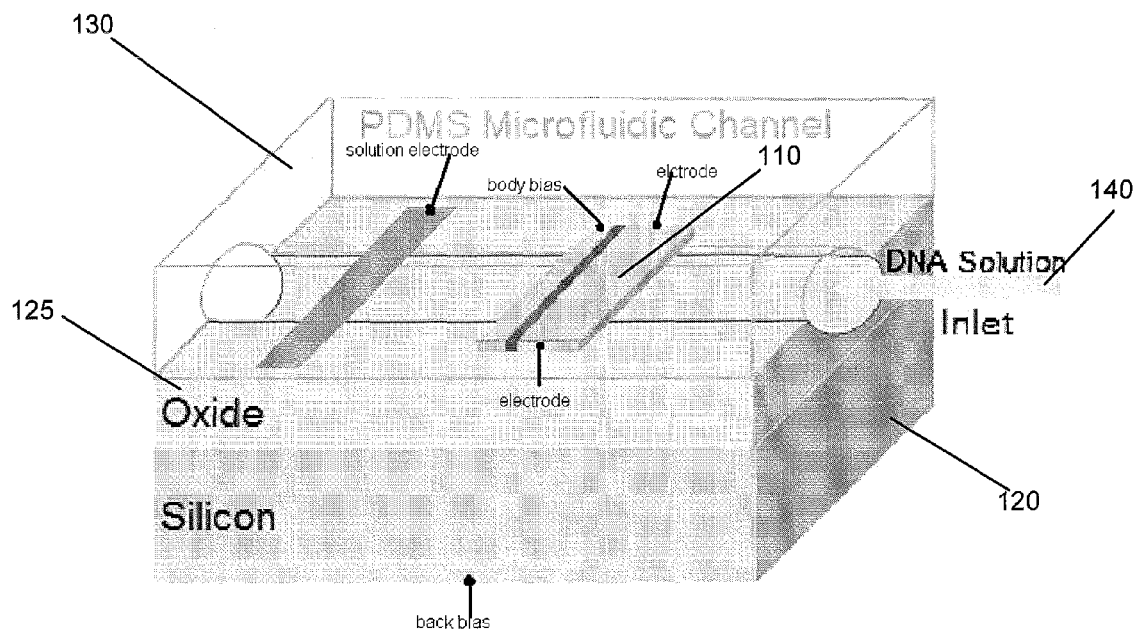
FIG. 1B shows another example embodiment of an apparatus for sensing biological materials including a microfluidic channel.

Turning now to the figures, FIGS. 1A and 1B illustrate an example embodiment of an apparatus constructed in accordance with the instant disclosure. As seen in the perspective views therein, the apparatus includes an SOI structure. In the embodiment shown, the SOI structure includes a silicon base 120, an insulative (e.g., oxide-based) layer 125 and a fluidics structure 130. In other embodiments, the layer 125 can be a semiconductor substrate with the same or opposite polarity as the three contiguous regions as above, or the SOI construction is used without removing/etching the Silicon at all (as in the case where the sandwiched region is accessed on only one of the two opposing surfaces). The fluidics structure 130 may be fabricated of PDMS ("Polydimethylsiloxane"). In one embodiment a fluidic channel 100 is defined by a portion of the upper-facing surface of the insulative layer 125 and by a bottom-facing surface of the fluidics structure 130. The semiconductor device 110, as seen in FIG. 1B, illustrates a fluid solution (inlet) 140 which may include target molecules to be sensed.

Figure 2:
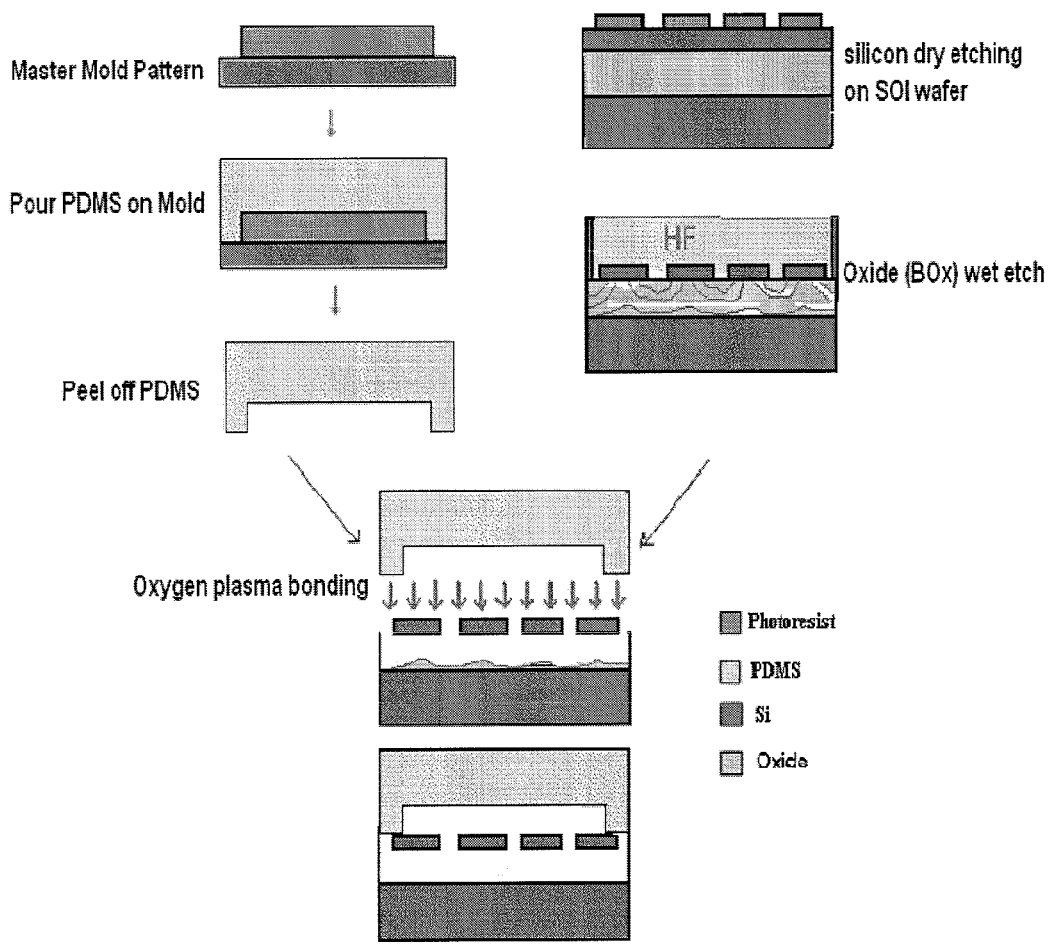
FIG. 2 shows an example embodiment of a method of manufacturing an apparatus for sensing biological materials.

Shown in FIG. 2 is a manufacturing process flow according to an example embodiment of the instant disclosure. The process includes an SOI wafer. In certain embodiments, the silicon thickness is approximately 100 nm, and buried oxide (BOX) thickness of 400 nm. One or multiple semiconductor devices are patterned onto the wafer using optical lithography. In certain embodiments, the length of each semiconductor device is approximately 40 μm, and the width can be adjusted from 300 nm to 500 nm, in other embodiments, the length and width can be varied; for example, the length may be from 40 μm to 100 μm or more, from 10 μm to 40 μm, from 1 μm to 10 μm, or may be less than 1 μm, and the width may be from 100 nm to 300 nm, from 30 nm to 100 nm, from 500 nm to 2 μm, from 2 μm to 10 μm, or more, or the width may be less than 30 nm as semiconductor manufacturing processes improve. In certain specific embodiments, there are 20 identical, parallel semiconductor sensors in each device. In other embodiments, there may be an array of semiconductor sensors in each device. There may be 20 to 500, 500 to 5,000, 5,000 to 50,000, 50,000 to 500,000, 500,000 to 5,000,000, 5,000,000 to 50,000,000, or more than 50,000,000 sensors in each device. The next step is to etch off the silicon area around the semiconductor devices done by dry etching. This is followed by another lithography step to define the place of the fluidic channel under the semiconductor devices. The semiconductor devices are also used as a mask for the wet etching of the buried oxide underneath them. Hence, a long channel with a depth of 400 nm (thickness of buried oxide) is etched out. In certain embodiments, the regions at the end of the bridges are implanted with boron to make a p+ or P++ region for the ohmic contact to the aluminum electrodes. Parallel to the fabrication process of the semiconductor devices, a mold for the fluidic channel is made. Liquid PDMS is poured into the mold and, once solidified, is peeled off from the mold substrate. The PDMS fluidic channel is then exposed to oxygen plasma, aligned to the wafer containing the bio-sensors and bonded to the wafer. In certain specific embodiments, the chip is left in a 70 C oven overnight for better PDMS to silicon oxide adhesion.

Figure 3:
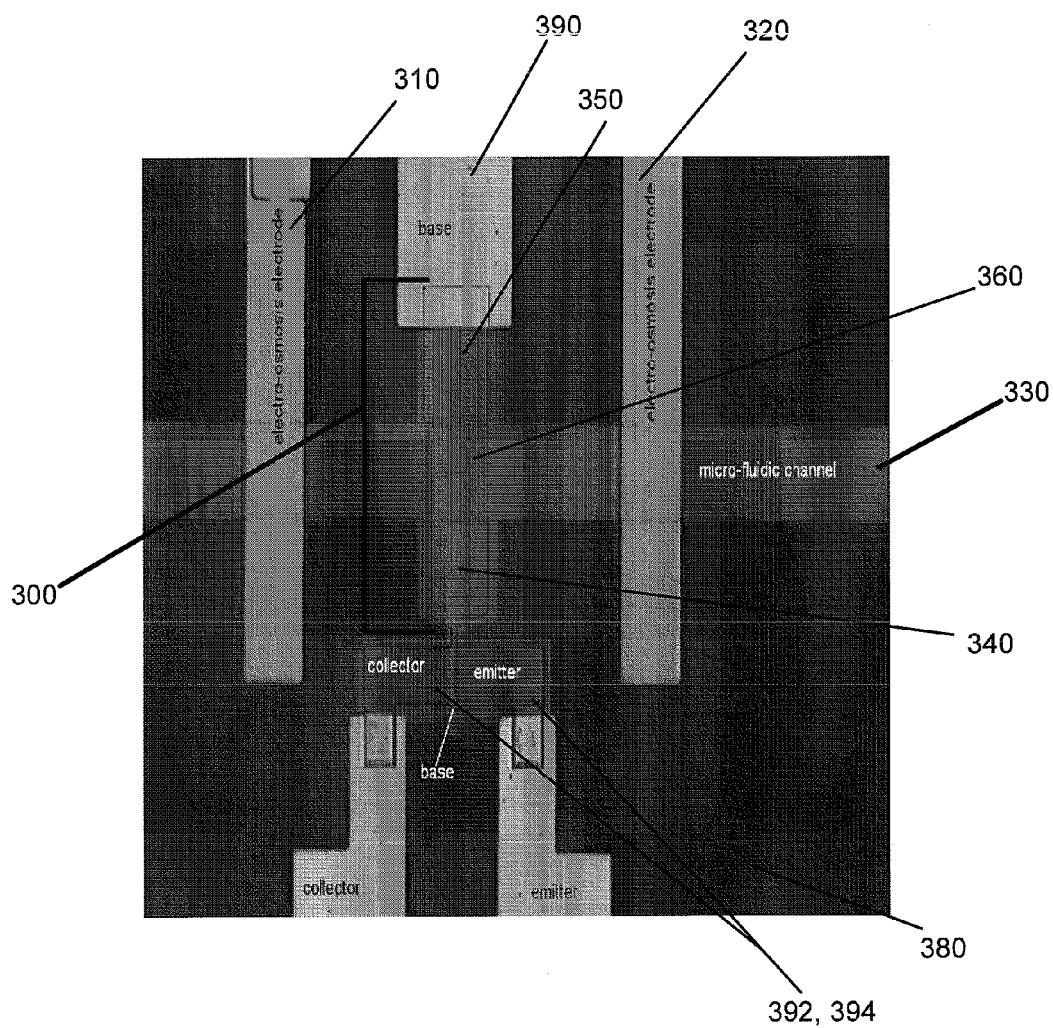
FIG. 3 shows an optical microscopy image of an example embodiment of an apparatus for sensing biological materials.

FIG. 3 shows another example embodiment of the apparatus for sensing target materials. The apparatus shown in FIG. 3 includes an SOI structure 380, and a fluidic channel 330 supported thereon. Also included is a semiconductor device 300. The semiconductor device 300 of this example embodiment includes three electrically-contiguous semiconductor regions, which are doped to a common polarity. The three electrically-contiguous semiconductor regions include a sandwiched region 360, and two outside other regions 340 and 350. As discussed above, the regions 340 and 350 are doped to a higher concentration than the sandwiched region 360. As can be seen in FIG. 3, the sandwiched region 360 has a surface directed toward the underneath fluidic channel 330. The fluidic channel 330 passes target materials through the channel, and target molecules may induce a voltage which change the surface potential of semiconductor and the sandwiched region may respond, by changing the conductance of said semiconductor region.

Also shown in FIG. 3, on the SOI structure 380, an amplification circuit which may comprise at least a bipolar transistor, including a base 390, a collector 392, and an emitter 394 which facilitates sensing of the target material flowing through the fluidic channel 330 by way of amplifying the current which passes through sandwiched semiconductor region 360. In other embodiments MOSFET, JFET or any other circuits known in the art may be used for amplification or readout. A metal electrode may be used to bring current into or out of SOI structure 380. FIG. 3 also shows the two other semiconductor regions 340 and 350 being electrically coupled (optionally) to electrodes 310 and 320 (discussed below in connection with FIG. 4). The electrodes 310 and 320 may be used to generate electrophoretic flow or electroosmotic flow.

The semiconductor device 300 may be arranged to respond to a bias voltage. The bias voltage may be applied to the target materials in the fluidic channel 330 by a reference electrode (not shown), or by back bias source (not shown), and said bias voltage will be added to the induced voltage resulting from target materials whereby the semiconductor device 300 senses the target materials in response thereto.

Figure 4A:
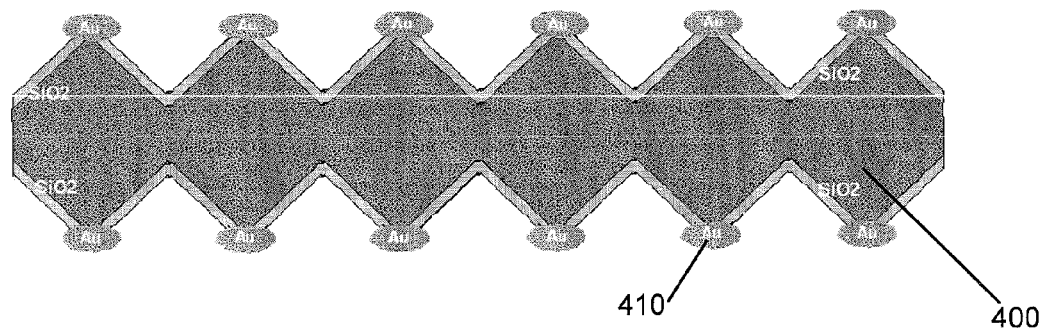
FIG. 4A shows an example embodiment of a biological sensor having a rough surface.
Figure 4B:
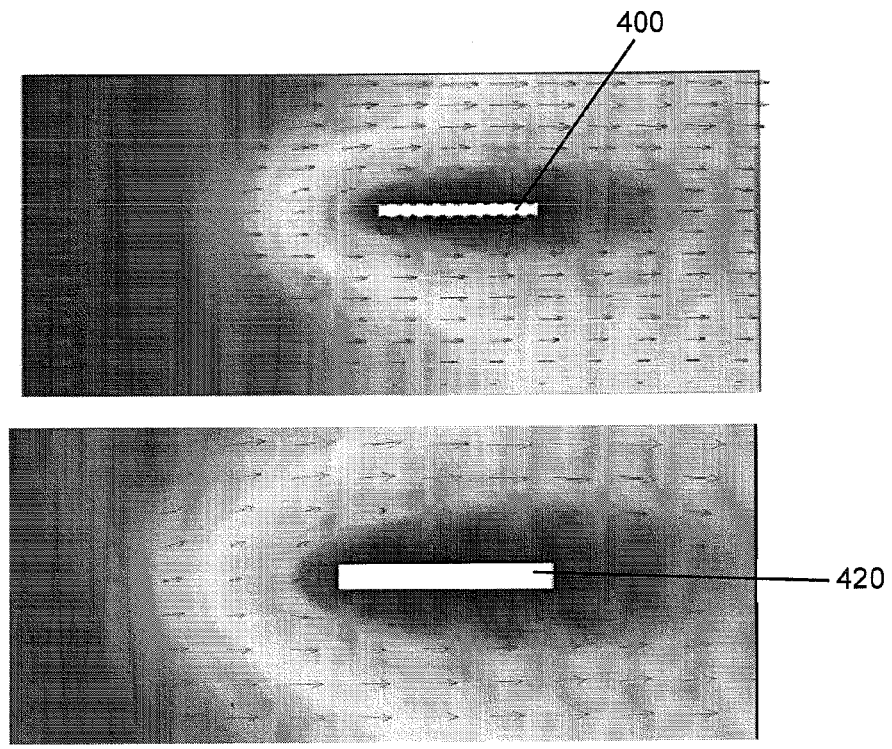
FIG. 4B shows a simulated rough-surface sensor and a smooth-surface sensor for DNA molecule concentration of a solution before and after passing the sensor.

In certain example embodiments, the surface of a semiconductor device directed toward the fluidic channel is roughened to increase sensitivity. Shown in FIG. 4A is a roughed version of the sandwiched semiconductor region 400. In certain specific embodiments, the roughened surface 400 includes beads or particles for adding roughness or for using as mask for etching and roughening the surface 410. Shown in FIG. 4B is a simulated concentration of target solution before and after passing the roughened surface 400 and the non-roughened surface 420.

Figure 5A:
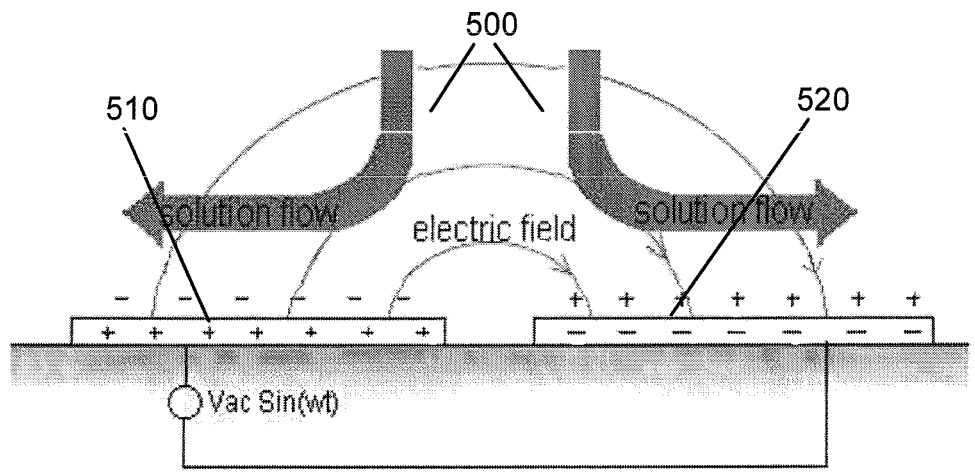
FIG. 5A shows an example embodiment of electro-osmosis through application of an AC signal on neighboring electrodes in an ionic solution.
Figure 5B:
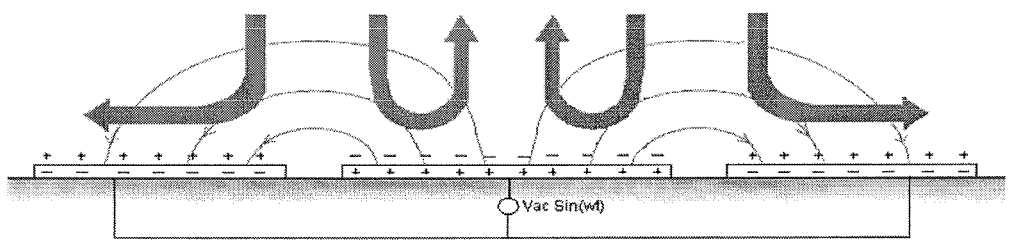
FIG. 5B shows an example embodiment of electro-osmosis and electrophoresis application around a biological sensor.

Shown in FIGS. 5A and 5B are examples of the electro-osmosis and electrophoresis application. FIG. 5A shows application of an AC signal on two neighboring electrodes 510 and 520 to create an electric-field solution flow 500. FIG. 5B shows a schematic of the electro-osmosis and the electrophoresis application, positioned around the sensor to circulate the flow and capture the negatively-charged target DNA molecules at the same time. By changing the cycle of AC signal, the direction of electro-osmosis force is not reversed and continues circulation in the same direction as the other half cycle of the AC signal.

Figure 6A:
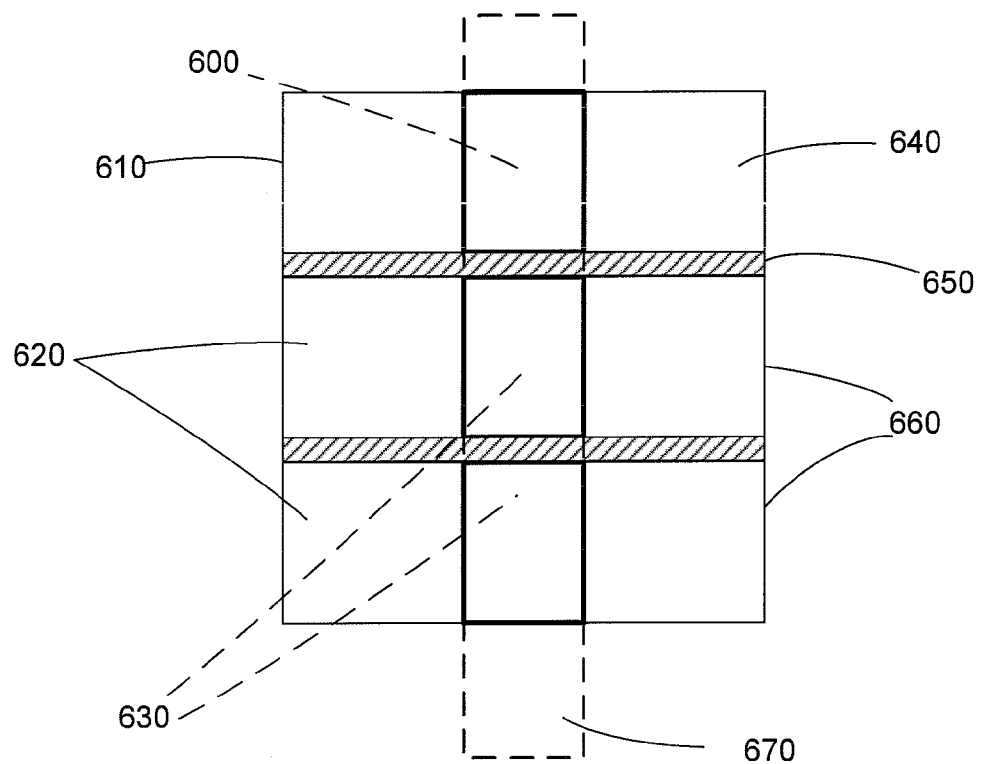
FIG. 6A shows an example embodiment of an apparatus for sensing biological materials including a microfluidic channel.
Figure 6B:
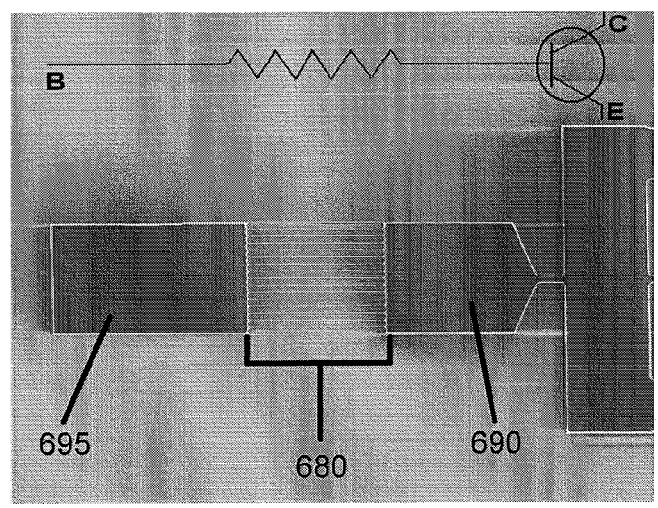
FIG. 6B shows an example embodiment of an apparatus for sensing biological materials including a microfluidic channel.

FIG. 6A shows an example embodiment of semiconductor devices in accordance with the instant disclosure. Three sets of three contiguous regions are shown in FIG. 6A as placed with respect to a fluidic channel 670. A first sandwiched region 600 is adjacent the fluidic channel 670. The first sandwiched region 600 includes a surface that is directed toward the fluidic channel 670 for sensing the target materials passed through the channel. Sandwiching the first sandwiched region 600 are a first end region 610 and a second end region 640. The first sandwiched region 600, the first end region 610, and the second end region 640 make up a first set of three contiguous regions. The first sandwiched region 600, the first end region 610, and the second end region 640 may be separated from at least one additional set of three contiguous regions by a dielectric layer 650. The additional sets of three contiguous regions include a first alternative end region 620, an alternative middle region 630, and a second alternative end region 660. Turning to FIG. 6B of an additional embodiment of the instant disclosure, a semiconductor device contains three contiguous regions. The contiguous regions include the sandwich region 680, which includes a comb-like structure, and connects the two other contiguous regions 690 and 695. The three contiguous regions of both embodiments shown in FIGS. 6A and 6B are doped to a common polarity. In certain example embodiments, the sandwich regions 600, 630, and 680 are doped to have a lower-dopant concentration than their respective other (outside sandwiching) regions 610/640, 620/660, and 690/695.

Various embodiments are directed to semiconducting nanobridge (or "nanowire") types of sensors, such as those including silicon, silicon of a silicon-on-insulator (SOI) structure, or other semiconductor material.

Other example embodiments are directed to the operation of a biosensor device. Phases of operation include: a loading phase in which probe biomolecules are attached or associated with a sensor, and a detection phase in which one or more target biomolecules, reaction products, or reaction byproducts have changed the local voltage generated or impressed on the nanobridge. The conductance of the nanobridge/nanowire is modulated during the loading and detection phases.

Aspects of the present invention are directed to modeling operational characteristics of a biosensor, and setting the characteristics according to the various modeling results. In many implementations, a bio-linker molecule such as APTES (10%), or ssDNA (1 $\mu$M), or a combination thereof, which may be used in combination with dsDNA, is used in a layer on a sensor device surface to achieve an effective or otherwise desirable charge and related threshold voltage shift, relative to the sensitivity of device to molecules such as dsDNA. Such an approach may involve, for example, using one or more aspects as discussed in T. Sakata, et al., Japanese Journal of Applied Physics, Vol. 44, No. 4B, pp. 2854-2859, 2005, which is fully incorporated herein by reference.

In various embodiments, a back bias voltage is used to set or otherwise influence the detection sensitivity of such a sensor, and can further be controlled to establish a condition sensitive to a particular target species, such as for use with a p-type silicon device under positive back bias voltage. One such implementation is shown in FIG. 3 of Appendix A filed in the underlying provisional application, showing an effect of an example back bias voltage application upon device sensitivity for a 10e13 (1/cc) P-type substrate. In various contexts, the effect of a back bias voltage in bringing the device to subthreshold region in SOI devices and increasing device sensitivity is stronger than in planar MOSFET devices.

Various embodiments are directed to using back bias as well as a charged biomolecule layer to modulate the Fermi level energy in an active area of device. This approach can be used to change (increase) the slope of Id-Vg curve, which is equivalent to sensitivity. Using this approach, the device can be operated in a desirable (e.g., sensitive) regime. Moreover, this regime can be tailored to sense specific biomolecules.

Various aspects of the present invention, as directed to the application of a bias via one or more gates or reference electrodes and as applicable to a back bias, may be implemented as follows. A positive charge associated with biomolecules is used to deplete hole carriers in a p-type sensor and increase the barrier height in the sensor channel, with a resulting drop in conductance. A negative charge associated with DNA may increase conductance. A back bias can be used in this context to control the conductance modulation. Alternatively, a bias may be applied by a combination of a reference electrode and a back bias.

Figure 5B:
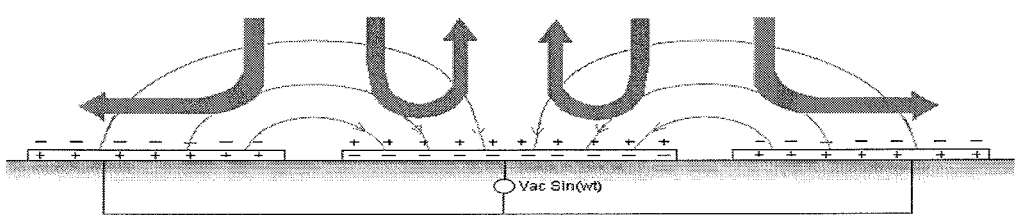

The various biosensors and biosensor devices as discussed herein may be fabricated using a variety of approaches. One such device is shown in FIG. 5 in Appendix A filed in the underlying provisional application, including an array of biosensors fabricated from a SOI wafer (e.g., with such a wafer having a top silicon thickness of about 50 nm).

Figure 7:
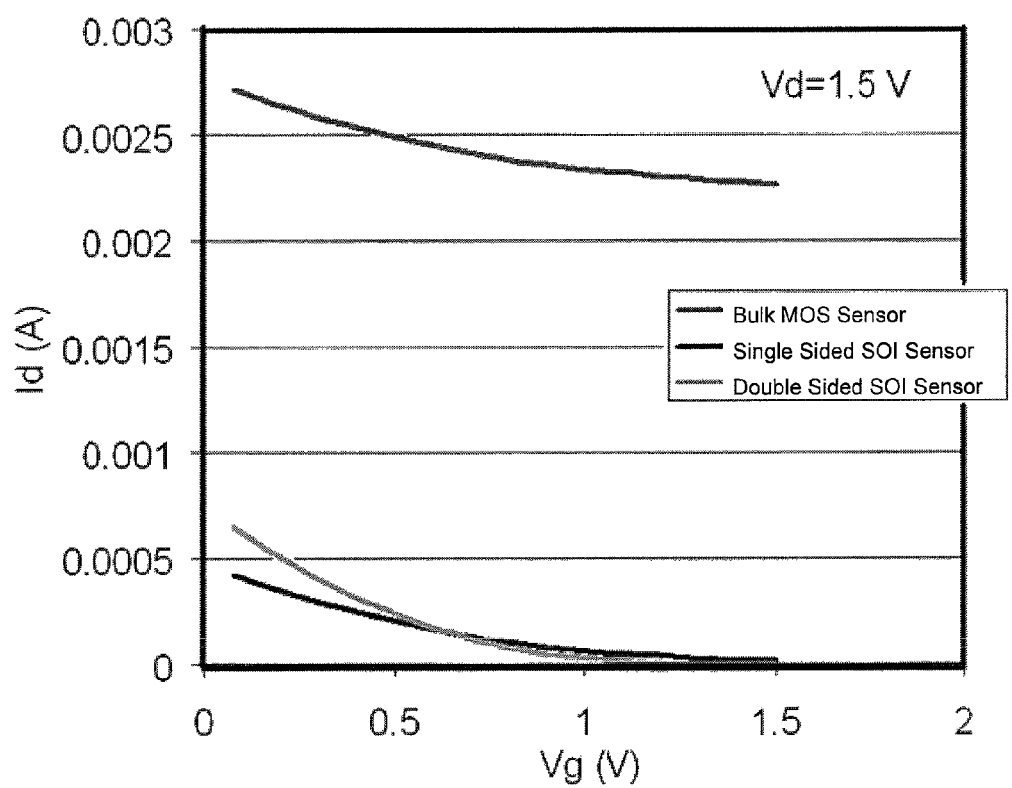
FIG. 7 is a graph showing electrical characteristics of three types of designs of embodiments consistent with the present disclosure.

For sensing DNA, different linkage molecules are used for attachment to sensor surfaces to achieve a desired charge density per unit area relative to each linkage molecule used and/or desired sensitivity. Various embodiments employ a nanobridge geometry (e.g., as shown in FIG. 1 of Appendix A), used as a planar sensor surface for detection and high sensitivity, via double-side exposure to target molecules such as DNA and/or protein. Planar biosensors can be manufactured with a relatively large width and be implemented with a relatively large signal current, achieving desirable noise reduction and a high signal-to-noise ratio (SNR). Various embodiments as shown in the Appendices describe conductance modulation via sensor functionalization, such as by DNA linkage molecules. Current-voltage (I-V) characteristics for such devices are shown, for respective embodiments involving specific concentrations of linkage biomolecules, including APTES, Strepavidin and Poly-L-Lysine (PLL), which have positive charge, such as shown in FIG. 7 of Appendix A, filed in the underlying provisional application. For the APTES molecules, an example solution includes 2% APTES in Ethanol or Aceton; for the Streptavidin molecules, an example solution includes 0.1 mg/mL streptavidin in PBS with 2 mM biotin solution. Such bio-species may be obtained, for example, from Sigma Aldrich Company of St. Louis, Mo.

Other example embodiments are directed to on-chip amplification of a signal produced via a biosensor and approach as discussed herein, to improve the signal-to-noise ratio. The detection signal, corresponding to conductance characteristics of a channel type region of a biosensor such as the previously described nanobridge as coupled to target molecules, is amplified. The noise can also be averaged as well. Such approaches may employ, for example, a Darlington or single amplifier. Other embodiments may utilize a more sophisticated amplifier and readout circuit, wherein row and column selection may be included as part of the amplifier circuit. The operational mode of the device may be implemented in the fully depleted, inverted, accumulated, enhanced or resistive mode depending on the concentration and operational circumstances, or the use of a BJT or MOS amplifier, such as discussed in one or more of the Appendices that form part of this document.

Example types of biosensor systems, as may be implemented in accordance with various embodiments, include a bio-species coated bead system and a direct binding system. In the direct binding system, the operation of the device has two main phases: a loading phase in which probe biomolecules (e.g., ss-DNA) are attached or associated with the sensor, and a detection phase in which a target bio-molecule (e.g., nucleotides) is attached or associated with the probe molecule. The conductance of the nanobridge/nanowire is modulated during the loading and detection phases.

Using the bead system approach, biomolecules (e.g., DNA or proteins) are attached or associated with a bead. The beads are then injected into the system and allocated adjacent to the biosensor. This allocation may involve, for example, manipulation of the flow of beads so as to introduce the bio-species molecules to the sensor. Various bimolecular interactions and reactions may then be monitored.

Accordingly, various example embodiments are directed to a sensor device having a planar array with on-chip amplification, as discussed herein. Various aspects are directed to large scale arrays of such sensors, which can be tailored to specific applications and set, or tuned, via the application of a bias. Such aspects can be used to achieve a desirable SNR and dynamic range, and are suitable for DNA sequencing and the detection of DNA, protein or other bio-species in microfluidic structures. Various embodiments use rough surface structure features to increase the sensitivity and SNR (e.g., as described in one or more of the Appendices forming part of this document).

For general information regarding sensors, and for more specific information regarding biosensors and related applications as may be implemented in connection with one or more example embodiments described herein, reference may be made to the following references, each of which is fully incorporated herein by reference: H. Esfandyarpour, NSTI-nanotech, Vol. 4, p. 421, 2007; J. Fritz, et al., PNAS, Vol. 99, No. 22, p. 14143, 2002; and C. M. Lieber, PNAS, Vol. 101, No. 39, p. 14017, 2004.

Experimental Embodiments

For any electrical device to be able to detect a charge, the charge should bind or associate to or near the device's surface and affect the electrical characteristics of the device. DNA molecules do not generally bind to oxide surfaces on their own. For this reason, linker molecules may be provided for their attachment thereto. These linker molecules could mediate DNA binding to the silicon oxide surface through physical or chemical forces. For instance, PLL, APTES and Streptavidin-Biotin are a physical (ionic) binding linker, while pHPMA binding to a surface may be a chemical (covalent) bond.

After functionalizing the surface of the sensor with the linker molecule, there will be a shift in the electrical characteristics of the sensor due to the induced charge of the linker layer on the surface of device and associated changes in the counter ions in the fluid. The first layer of DNA, called probe DNA, will induce another change (shift) in the electrical characteristics and counter ion electrical characteristics. A solution containing the sample DNA is then introduced into the system using simple fluidics and it is tested for complementarity to the probe DNA. If the sample contains the complementary strand, it will hybridize to the probe DNA attached to the sensor and induce a secondary shift in the electrical response curve, and the thus the conductivity of the nanosensor.

Usually this second shift is smaller than the first one, which could be due to the fact that double-stranded DNA is rigid in contrast to single-stranded DNA which is more flexible. The rigidity of the double-stranded DNA will result in a greater average physical distance between the DNA and the surface of the sensor and hence it will lower the effect on the change in conductivity of the device (see A. Poghossian, A. Cherstvy, S. Ingebrandt, A. Offenhausser, M. J. Schoning, *Possibilities And Limitations Of Label-Free Detection Of DNA Hybridization With Field-Effect-Based Devices*, Sensors and Actuators B 111-112, 470-480 (2005)). In addition to the rigidity of double-stranded DNA, there is always a possibility that there is interference with the binding of the sample DNA to the probe DNA because of the already highly functionalized and charge-modified surface of the sensor. This could be a result of the coulomb repulsion between two negatively-charged DNA molecules. For any electrical device to be able to detect a charge, charge should bind or associate to or near the surface of the device. The negative charge of bound DNA molecules will affect current or conductance of a device.

An electrical sensor should have a high surface-to-volume ratio in order to have the highest possible signal in response to a charge modulation on or near the surface. The sensor should have an easily measurable signal-to-noise ratio because the change in electrical signal due to the charge modulation is usually only a few percent of a base-line reference current. For best signal to noise ratio, in addition to the need for a large surface-to-volume ratio, the active area of the sensor should also be as large as possible to capture as many DNA molecules or other target moieties as possible.

In one embodiment, a nanowire sensor as described herein has a rod structure with high aspect ratio. The nanowire may be comprised of a doped semiconductor and can be formed through chemical vapor deposition, lithography or other methods known in the art. The nanowire sensor device may have three elements. Two conductive formed regions and the insulator or low conductivity gap between the two regions. The conductive regions can be made of highly doped semiconductor or metal, through photolithography.

There are two designs that could be proposed for such a sensor: an array of nanowires; and an array of parallel suspended plates. The first design consists of an array of vertical or horizontal nanowires (with the sensor structure along a largely horizontal plane), in which the direction of the solution flow is perpendicular to the nanowires. DNA molecules or other moieties will bind or associate to or near the functionalized nanowires and change the conductance due to their charge. In the second design, an array of parallel nanobridges makes up the sensor. As solution flows through the channel, DNA molecules or other moieties will bind or associate to or near both sides of the bridges, top and bottom, similar to a double gated device. The charge of the DNA molecules or other moieties will cause accumulation or depletion of more holes in the bulk of a p-type sensor and hence increase its conductance.

Conductance of the sensor will also change after functionalizing the sensor surface. This change depends on the charge of the linker molecule layer. If negative, the bulk of the p-type sensor will accumulate holes and conductance will increase. On the other hand, if positive, conductance will decrease due to the hole depletion. Linker molecules usually have a positive charge, especially when they are binding DNA covalently, therefore the conductance of the sensor will decrease at the time of functionalization.

The sensor is designed to be sensitive enough to detect low concentrations of DNA and at the same time highly effective at capturing the sample or target DNA molecules in order to detect binding. To compare which design is better for capturing the DNA molecules, the total number of DNA molecules bound to the sensors was compared using COMSOL simulation. In this simulation, the nanowire and nanobridge designs are compared with each other. Both sensors have the same total surface area and the same surface-to-volume ratio.

The reaction at the active surface is given as in Equation 2.1:

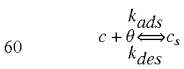

Where c is the bulk concentration, $\theta$ is the surface concentration of active sites, $c_s$ is the surface concentration of adsorbed species (moles per unit surface), $k_{ads}$ is the rate constant for the forward reaction, and $k_{des}$ is the rate constant for the backward reaction.

This simulation assumes the following values regarding the hybridization kinetics of DNA on surface and the diffusion rate on surface and solution (see, e.g., Hong Shen et al., DNA Diffusion in Mucus: Effect of Size, Topology of DNAs, and Transfection Reagents, Biophysical Journal Volume 91 July 2006 639-644; and J. R. Pascault, A Finite Element Study of the DNA Hybridization Kinetics on the Surface of Microfluidic Devices, A thesis submitted to the faculty of the Worcester Polytechnic Institute):

$k_{des}$=6×E-5 s-1
$k_{ads}$=6×E4 M-1 s-1
Convection & diffusion for particles movement
Vo=1E-3 m/s
D=1E-9 m2/s
Ds=0
Bo=1E-3 moles/m2
$k_{ads}$: the rate constant for the backward reaction,
$k_{des}$: the rate constant for the forward reaction,
Vo: the velocity of incoming fluid,
D: the diffusion rate of DNA molecules thorough the solution,
Ds: the diffusion rate of DNA molecules on the surface of sensor,
Bo: the density of bonded DNA molecules on the surface.

For having equilibrium in the adsorbed material, $c_s$, on the surface of the sensor device, the equation governing the surface diffusion and the surface reaction rate is shown in Equation 2.2:

$$\frac{\partial c_s}{\partial t} + \nabla \cdot (-D_s \nabla c_s) = k_{ads} c\theta - k_{des} c_s$$

where $D_s$ is surface diffusivity. However, the concentration of active sites is equal to the difference between the total number of active sites and the number of sites that are occupied by the adsorbed molecules, therefore, the equation for the rate reaction is given by Equation 2.3:

$$\frac{\partial c_s}{\partial t} + \nabla \cdot (-D_s \nabla c_s) = k_{ads} c(\theta_0 - c_s) - k_{des} c_s$$

where $\theta_0$ is the total number of active sites available on the surface of the sensor. The initial condition of this equation is that the concentration of the adsorbed species on the surface of the sensor is zero at the beginning of the process ($c_s$(t=0)= 0). The equation for the surface reaction includes the concentration of the bulk species, c, at the top of the sensor surface. The equation must be solved for the surface reaction in combination with the mass balance in the bulk. The transport in the bulk of the channel is described by a convection-diffusion equation, Equation 2.4:

$$\frac{\partial c}{\partial t} + \nabla \cdot (-D\nabla c + cu) = 0$$

where c is molecule concentration at the channel, D is the diffusivity of those molecules in the channel, and u is the velocity vector.

The initial condition for c is set so that the bulk concentration is equal to $c_0$ at the beginning of process (c(t=0)=$c_0$). The adiabatic condition for all the surfaces except the inlet, outlet and the sensor surface for the material balance is:

$n \cdot (-D_s \nabla c_s)$=0

The boundary condition at the sensor surface couples the rate of the reaction at the surface with the flux of the binding molecules, the concentration of the adsorbed molecules and the concentration of the molecules in the bulk:

$n \cdot (-D\nabla c + cu) = k_{ads} c(\theta_0 - c_s) k_{des} c_s$

The boundary conditions for the inlet and outlet are:
Inlet: C=$c_0$
Outlet: $n \cdot (-D\nabla c + cu) = n \cdot cu$
The boundary condition for the other surfaces except for the sensor is (adiabatic):

$n \cdot (-D\nabla c + cu) = 0$

The number of DNA molecules bonded to the planar sensors was approximately 1.6 E-15 (moles/cm$^2$), and approximately 3.71 E-16 (moles/cm$^2$) for the nanowire sensor (see, e.g., Manual of COMSOL Multiphysics). Nanowire sensors captured less DNA molecules due to their geometry, as the DNA-depleted solution passing the first rows in nanowire array hits the rest of nanowires and decreased the number of possible capturable DNA molecules.

The following discusses various design types of bio-sensor devices. One type can be classified as a bulk MOS device, based on p-type silicon construction and with an electrical connection through a highly p-type region to two ohmic contacts. A second type is a single-sided SOI MOS device that keeps the sandwiched semiconductor region intact but has a very thin layer of silicon below the said sandwiched semiconductor region. A third double-sided SOI type has a fluidic access to both sides of sandwiched semiconductor region. In other embodiments the MOS (metal oxide semiconductor) structure can be configured without metal layer or in other embodiments without this insulating layer or a combination of the two.

Electrical characteristics of these three designs was simulated by applying a voltage bias to one of the two end semiconductor regions and another sweeping voltage to the sandwiched semiconductor region, and measuring the passing current at the same time by an MEDICI simulator. As can be seen from the curves, shown in FIG. 7, the first design (bulk MOS sensor) exhibits the highest level of current due to the thick bulk but very shallow slope for the Id/Vg characteristics. The third design, i.e., double sided structure, has the steepest slope and the highest second derivative of the Id/Vg characteristics. A steeper slope means that by modulating the charge on the sandwiched semiconductor region (DNA charge), there will be a larger current change (higher sensitivity to charge modulation) and the higher second derivative means that the ratio of the current change in response to target DNA hybridization and the probe DNA immobilization is higher (more change in current after hybridization).

The effective charge of DNA on the sensor surface after probe immobilization and target hybridization can be calculated from the experimental data from others' electrical DNA detection experiment results, as is well known.

By importing this data into the MEDICI device simulator, the ratio of conductance change in target hybridization and probe immobilization can be found for these three devices. The double gated SOI MOS sensor has the highest ratio for the conductance change. It is proposed that a sensor is positioned on an etched channel in the substrate and there is a PDMS micro-fluidic device with a fluidic channel formed therein on top of the sensor. Therefore, the sensor is suspended between two fluidic channels (one on top and one at the bottom) and DNA molecules can bind to both sides of the thin sensor, making it like a double gated SOI MOS sensor.

The bio-sensor should be able to detect an ionic solution flowing through the channel when the top micro-fluidic channel is bonded to the sensor substrate. When the pH of the solution increases from a neutral or low pH, hydroxide ions which are bound or associated with the surface of the sensor accumulate holes near the p-type sensor surface. This leads to an increase in the number of carriers and consequently an increase in conductance. On the other hand, by decreasing the pH of the solution, a reduction in the number of hydrogen ions bound or associated with the surface of the sensor will deplete holes near the p-type sensor surface so that the conductance of the sensor decreases.

Experimental tests of the sensor with different pH solutions and different functionalizing linker molecules showed that by increasing the pH of the solution, there is an increase in the conductance. When the sensor is dry, its current is around 40 uA. By flowing a PBS buffer having a pH of 7, there is an increase in conductance. This increase is due to the difference between the work function of air and the work function of the solution that causes an accumulation of holes in the p-type sensor surface, and or as a result of binding of hydrogen ions to the surface of the sensor.

When the device surface is functionalized with APTES, a physical linker molecule, conductance of the sensor decreases because of the positive charge of the APTES layer that depletes the holes from sensor surface. On the other hand, Streptavidin, a slightly negatively-charged linker molecule, slightly increases the current of the sensor due to the charge of the linker layer. Streptavidin has almost no effect on the current of the sensor when it flows through the channel with an APTES coated sensor. This implies that the charge of Streptavidin is almost negligible in comparison to the charge of the APTES layer. However, there is also the possibility that the layer of Streptavidin is not close enough to the surface of the sensor to be able to affect its charge distribution because the APTES already coats the surface of the sensor with around 3-8 mono-layers. The distance that a charged molecule needs to be within to cause a significant effect on the sensor is a function of the Debye length, and thus of the ionic concentration of the fluid in the volume adjacent the sensor.

In order to detect DNA hybridization, the sensor surface should be functionalized with immobilized probe DNA. By flowing the target DNA solution through the channel, the device will detect whether the DNA is complementary or non-complementary. When two strands of DNA are complementary, they will react and bind to each other. This binding will increase the negative charge on the surface, because there are two strands of DNAs on the surface instead of one. This increase in negative charge increases the conductance of the sensor by accumulating more holes near the surface of the sensor. When two strands are not complementary, they do not bind to each other and the charge on the surface will not change. However, there is usually an increase in conductance even when the target DNA is not complementary to the probe DNA. This is due to the functionalizing layer, which is positively-charged. The charge of the linker molecule layer compensates the negatively-charged non-complementary DNA through coulomb interaction. Hence, an increase in current is detected.

The sensitivity of the bio-sensor can be increased by enhancing the number of captured molecules or by enhancing the signal-to-noise ratio.

A bipolar junction transistor (BJT) can be used as AC or DC amplifier. A BJT is a three terminal device with a "base", "emitter" and "collector" made of doped semiconductor (e.g., NPN bipolar transistor). The direction of current flow from the sensor is always between the base terminal and emitter terminal. Both electrons and holes transports are involved in the operation of bipolar junction transistors. Electrical current is generated by diffusion of charge carriers from one region to the other two regions with different charge concentration.

In active mode operation, the base-emitter junction diode is forward biased and the base-collector junction diode is reverse biased. In an NPN transistor, for example, when a positive voltage is applied to the base-emitter junction, the equilibrium between thermally generated carriers and the repelling electric field of the depletion region becomes unbalanced, allowing thermally excited electrons to inject into the base region. These electrons diffuse through the base from the region of high concentration near the emitter toward the region of low concentration near the collector. In the collector and the emitter, holes are minority carriers because they are n-type doped, so that the electrons are majority carriers. On the other hand, the electrons in the base are minority carriers because the base is p-type doped.

To minimize the recombination of carriers that are crossing the base before reaching the base-collector junction, the transistor's base region must be thin enough that carriers can diffuse across in a time less than the minority carrier's lifetime in the base, and the base thickness must be less than the diffusion length of the minority carriers in the base (e.g., electrons in a NPN bi-polar junction transistor). The collector-base junction diode is reverse biased in active mode, and a small number of electrons come from the collector to the base, but electrons that diffuse from the emitter (and generated ones in base) to the base towards the collector are swept into the collector by the electric field in the depletion region of the collector-base junction. The currents in BJT terminals can be controlled so that they are exponentially-dependent on the base-emitter voltage. Since the base-collector junction diode is reverse biased in the active mode operation, the base-collector voltage does not have much of an effect on the emitter-collector current. The common emitter current gain, $\beta_F$, is approximately the ratio of the DC collector current to the DC base current in the forward-active region. The current gain, $\beta_F$, is given by:

$$\beta_F = \frac{I_C}{I_B}$$

For the fabricated BJT, this ratio was around 30. By increasing the base voltage, collector current increases, and by binding DNA to the surface of the sensor, collector current again increases due to accumulation of holes in the sensor surface region. When conductance of the sensor in series with the base increases, the current passing through the collector increases as well.

If lower concentrations of DNA are used, there will be fewer DNA molecules bound to the sensor. In order to increase the number of DNA molecules bound to the sensor, thereby improving the sensor signal, more DNA can interact with the DNA bound or associated with the surface of the sensor by dielectrophoresis and electro-osmosis forces.

Electrophoresis is the motion of dispersed particles relative to a fluid under the influence of an electric field. The dispersed particles have an electric surface charge, on which an external electric field exerts an electrostatic coulomb force. According to the double layer theory, all surface charges in fluids are screened by a diffuse layer of ions, which has the same absolute charge but opposite sign with respect to that of the surface charge. The electric field also exerts a force on the ions in the diffuse layer, that force having a direction opposite to the force acting on the surface charge. The force of the electric field is applied to both the particle and to the ions in the diffuse layer that are located at some distance from the particle surface. Through viscous stress, part of the electric force is transferred to the particle surface. This part of the force is also called electrophoretic retardation force. The electrophoretic retardation force may be greater than or less than the electrostatic force which also acts on the particle.

Electroosmotic flow is the motion of liquid induced by an applied potential across a material, capillary tube, membrane, channel (or microchannel), or any other fluid conduit. Because electroosmotic velocities are independent of conduit size, as long as the double layer is much smaller than the characteristic diameter scale of the channel, electroosmotic flow is most significant in small channels. Electroosmotic flow is an essential component in chemical separation techniques. Electroosmotic flow is caused by the Coulomb force induced by an electric field on a net mobile electric charge in a double layer. Because the chemical equilibrium between a solid surface and an electrolyte solution typically leads to the interface acquiring a net fixed electrical charge, a layer of mobile ions, known as an electrical double layer or Debye layer, forms in the region near the interface. When an electric field is applied to the fluid (usually via electrodes placed at inlets and outlets), the net movement of charge in the electrical double layer is induced by the resulting Coulomb field. The resulting flow is termed electro-osmotic flow.

DNA concentrators using AC electroosmosis have been developed to concentrate large molecular weight molecules. Hence, electrophoresis, which is the most well-known electro-kinetic phenomenon, can provide an attractive force to hold small charged particles. AC electro-osmosis can generate bulk fluid flow to transport single-strand DNA molecules from a large effective volume to the electrode surface. Electrophoresis can attract single-strand DNA molecules and hold them on the electrode surface simultaneously. When an electric field generated by the two electrodes is applied tangentially to a surface bathed in electrolytes, the charges in the electrical double layer experience a force. Consequently, the fluid is pulled along the charges and bulk fluid flow is generated. Electric potential causes charges to accumulate on the electrode surface, creating a charge density that forms the electrical double layer. The double layer interacts with the tangential component of the electric field to induce fluid motion along the electrode surface. AC electro-osmotic flow can be induced by an AC electric field on microelectrodes in the frequency ranges below the charge relaxation frequency. At a relatively-low frequency, most of the potential drop occurs in the double layer. The electric field is at a minimum and a small slip velocity is generated along the surface. At a high frequency, the charges in the double layer are less and slip velocity tends to be zero. Accordingly, the maximum slip velocity occurs at an intermediate frequency. For further information in this regard, reference may be made to: A. Ramos, H. Morgan, N. G. Green, A. Castellanos, *AC electric-field-induced fluid flow in microelectrodes*; J Colloid Interface Sci 217:420-422, 1999; M. R. Bown AE C. D. Meinhart, *AC electroosmotic flow in a DNA concentrator*, Microfluid Nanofluid (2006) 2: 513-523; D. Stein, Z. Deurvorst, F. H. J. van der Heyden, W. J. A. Koopmans, A. Gabel and C. Dekker, *Electrokinetic Concentration of DNA Polymers in Nanofluidic Channels*, Nano Lett. 2010, 10, 765-772; H. ChengKin, F. Lei, K. Ying Choy, L. M. C. Chow, *Single-stranded DNA concentration by electrokinetic forces*, J. Micro/Nanolith. MEMS MOEMS 8_2_, 021107, 2009; K. Fong Lei, H. Chenga, K. Ying Choyb, L. M. C. Chowb, *Electrokinetic DNA Concentration in Microsystems*, Sensors and Actuators A 156 (2009) 381-387.

Simulation of generation of electro-osmotic flow has been done for three parallel electrodes in an ionic solution. The center electrode has a different applied voltage from the other two, and the other two electrodes are short-circuited to each other and have the same voltage bias. Some assumptions that have been used for the simulation are:

$\rho$ 1000 kg/m3 Density of the fluid
$\eta$ 10-3 Pa·s Dynamic viscosity of the fluid
$\in_r$ 80.2 Relative electric permittivity of the fluid
$\zeta$ -0.1 V Zeta potential on the wall-fluid boundary
$\sigma$ 0.11845 S/m Conductivity of the solution
D 10-11 m$^2$/s Diffusion coefficient
Vac 4V AC voltage
W 1000 Hz frequency The Navier-Stokes equations for incompressible flow describe the flow in the channels:

$$\rho \frac{\partial u}{\partial t} - \nabla \cdot \eta (\nabla u + (\nabla u)^T) + \rho u \cdot \nabla u + \nabla p = 0$$

$$\nabla \cdot u = 0$$

Here $\eta$ represents the dynamic viscosity (kg/(m·s)), u is the velocity (m/s), $\rho$ equals the fluid density (kg/m3), and p refers to the pressure (Pa). It is assumed that the flow has a fully developed laminar profile at the inlet channel. It is also assumed that at the outlet boundary fluid flows out freely and the stress components at this boundary are zero.

$$n \cdot [-pI + \eta (\nabla u + (\nabla u)^T)] = 0$$

Most of the solid surfaces in contact with an electrolyte form a surface charge, and a double layer charge forms at the electrolyte/solid surface interface in response to the spontaneously formed surface charge. The electric double layer forms because of the surface charges in the solution/solid interface. By applying a voltage, the electric field generates the electro-osmotic flow that displaces the charged liquid in the electric double layer. The electric force on the positively-charged solution close to the interface makes the fluid start to flow in the direction of the electric field.

The thin electric double layer was replaced by the Helmholtz-Smoluchowski relation between the electro-osmotic velocity and the tangential component of the electric field in all boundaries except for the inlet and outlet:

$$u = \frac{\varepsilon_w \zeta_0}{\eta} \nabla_T V$$

Where $\in_w$ represents the fluid's electric permittivity (F/m), is the zeta potential at the channel wall (V), and V is the applied potential (V).

The balance equation for current density is expressed by Ohm's law. If there is no gradient in the concentration of ions carrying the current, the divergence of the current density is set to zero:

$$\nabla \cdot (-\sigma \nabla V) = 0$$

where $\sigma$ is conductivity (S/m). The electric potentials on the center electrode are sinusoidal in time with the maximum value of 4 V and the frequency of 800 Hz. The adiabatic boundary condition on all boundaries except for the electrodes is that the normal component of electric field is equal to zero:

$$-\sigma \nabla V \cdot n = 0$$

The concentration of DNA molecules is increased after applying the DC and AC signal to capture them.

There are techniques to chemically bind the DNA to a specific surface. To immobilize probe DNA to a silicon oxide surface, a layer of APTES is often used. APTES is known for covalently binding to silicon oxide but not to silicon nitride. In order to be able to bind DNA molecules to the sensor's surface but not to other areas of the channel, silicon oxide is used for the gate dielectric of the sensor while all other surfaces in the micro-fluidic channel are covered by a layer of silicon nitride which was deposited by a chemical vapor deposition technique with a thickness of approximately 100 nm.

By flowing a solution containing 10% of APTES in ethanol, APTES molecules covalently bound to the silicon oxide but not to the silicon nitride. All surfaces then were washed with ethanol to remove any residue and unbound APTES molecules in the channel. Probe DNA with a concentration of 1 uM in PBS was then introduced into the channel. In aqueous solutions, silicon nitride reacts with water and forms silica, silanol and ammonium groups. The ammonium dissolves in water and increases the local pH of the solution from pH 6-7 to pH 9-10. Silicon nitride surfaces are negatively-charged in alkaline solutions (pH 9-10) since the isoelectric point of silicon nitride is between 5 and 6. Negatively-charged probe DNA molecules are covalently bound to the APTES coated silicon oxide surface. After the functionalization step, the micro-fluidic channel is washed with PBS buffer. DNA molecules in this step are labeled with EDC (N-(3-Dimethylaminopropyl)-N'-ethylcarbodiimide hydrochloride). The procedure for modifying 5' phosphate groups to enable covalent binding is:

1. Dissolve ethylenediamine (or alternative) to a final concentration of 0.25 M in 10 μl of 0.1 M imidazole.
2. Weigh 1.25 mg (6.52 μmol) of EDC into a micro-centrifuge tube.
3. Add 7.5 μl of the prepared oligonucleotide to the tube containing the EDC and immediately add 5 μl of the ethylenediamine/imidazole solution.
4. Vortex tubes until contents are completely dissolved, and then briefly centrifuge the tube to gather contents.
5. Add an additional 20 μl of 0.1 M imidazole, pH 6.
6. Incubate reaction at room temperature overnight,
7. Remove non-reacted EDC and the by-products, and imidazole by dialysis (e.g., Slide-A-Lyzer® MINI Dialysis Units) or spin desalting column (Zeba™ Desalt Spin Column) using 10 mM sodium phosphate, 0.15 M NaCl, 10 mM EDTA, pH 7.2, or other suitable buffer.

A solution of 10 uM BSA in PBS buffer is then flowed through the channel. Since BSA is a very sticky molecule, it binds to almost any clean surface. In the channel, BSA molecules will bind to silicon nitride but not to silicon oxide surfaces, which are already coated and saturated with APETS and the probe DNA molecules. The channel is then washed with PBS buffer to remove BSA molecules that did not bind to any surface.

Low concentration target DNA molecule solution for detection is flowed into the micro-fluidic channel. Target DNA molecules will bind to the probe DNA molecules when they are complementary. Since probe DNA molecules are already bound to the bio-sensor surface, target DNA molecules will also bind to the surface through the complementary DNA bound to said surface. DNA molecules are mainly bound selectively to silicon oxide rather that silicon nitride, as the BSA largely prevents nonspecific binding to the silicon nitride surfaces.

Another way to enhance the number of DNA molecules bound to the sensor surface is by increasing its effective area. This can be done by increasing surface roughness so that the magnitude of roughness is on the order of the DNA molecule size. A proposed way to achieve surface roughness on the order of 10 nm-20 nm is by etching silicon on a gold nanoparticle mask. A silicon surface could be etched by a KOH solution at room temperature. The etch rate of silicon by cold KOH is around 10 nm/min (see, e.g., K. R. Williams and R. S. Muller, *Etch Rates for Micromachining Processing*, Journal Of Microelectromechanical Systems, Vol. 5, No. 4, December 1996).

In order to compare the capture rates in rough and smooth surfaces, COMSOL simulation was used. The assumptions behind these simulations are:
Kads=6×10E4 M−1 s−1
Kd=Kads/Kdes=10E9 M−1
Kdes=6×10E-5 s−1
Vo=10E-3 m/s
D=10E-9 m²/s
Ds=0
Bo=10E-3 moles/m²

Kads: the rate constant for the backward reaction; Kdes: the rate constant for the forward reaction; Vo: the velocity of incoming fluid; D: the diffusion rate of DNA molecules thorough the solution; Ds: the diffusion rate of DNA molecules on the surface of sensor; Bo: the density of bonded DNA molecules on the surface. The main assumptions for these simulations are convection, diffusion and chemical adsorption, as described by Longmuir equation.

$$\partial b/\partial t = k_{on}c_s(b_m - b) - k_{off}b$$

The relationship of binding density and location on the sensor surface at different times relates to the integral of the binding curves as a function of time and location, which yields the total number of bound DNA molecules. After 10 minutes, the smooth surface bound 1.6 E-16 (moles/cm²) and the rough surface bound 2.06 E-10 (moles/cm²), which corresponds to around 25% more DNA molecules than on the smooth sensor.

Various embodiments described above, characterized in the claims and/or shown in the figures may be implemented alone, together and/or in other manners. One or more of the items depicted in the drawings/figures can also be implemented in a more separated or integrated manner, or removed and/or rendered as inoperable in certain cases, as is useful in accordance with particular applications. For example, the various discussions of field-effect transistors and other devices may be implemented with different field-effect devices, using approaches as described herein. In view of the description herein, those skilled in the art will recognize that many changes may be made thereto without departing from the spirit and scope of the present invention.

What is claimed is:
1. An apparatus for sensing target materials including biological or chemical molecules in a fluid, the apparatus comprising:
 a semiconductor-on-insulator (SOI) structure including an electrically-insulating layer;
 a fluidic channel supported by the SOI structure and configured and arranged to receive and pass a fluid including the target materials;

at least two electrodes configured and arranged to pass current for facilitating electrophoretic flow or electroosmotic flow of the fluid through the fluidic channel;

a semiconductor device including at least three electrically-contiguous semiconductor regions doped to exhibit a common polarity and located in the fluidic channel, the semiconductor regions including a sandwiched region sandwiched between two of the other semiconductor regions, and configured and arranged adjacent to the fluidic channel with a surface directed toward the fluidic channel for coupling to the target materials in the fluidic channel, and further arranged for responding to a change in potential;

said two of the other semiconductor regions being configured and arranged at least partially on the electrically-insulating layer, being doped at a higher concentration than the sandwiched region and being electrically connected to end electrodes, wherein in response to the potential resulting from the target materials in the fluidic channel, said at least one contiguous semiconductor region is configured and arranged to sense the presence of the target materials in the fluidic channel in response to the flow of electrons in a conducting mode from one end electrode to another end electrode; and an amplification circuit supported by the SOI structure and configured and arranged to facilitate sensing the target material near or in the fluidic channel.

2. The apparatus of claim 1, wherein the conducting mode is a depletion mode.

3. The apparatus of claim 1, wherein the conducting mode is an accumulation mode.

4. The apparatus of claim 1, wherein said at least one contiguous semiconductor region is configured and arranged to sense the presence of the target materials in the fluidic channel by at least one of: transitioning from a non-conducting mode to the conducting mode; and modulating the conductivity in the conducting mode.

5. The apparatus of claim 1, wherein the common polarity of the at least three contiguous semiconductor regions is a p-type doping scheme.

6. The apparatus of claim 1, wherein the common polarity of the at least three contiguous semiconductor regions is an n-type doping scheme.

7. The apparatus of claim 1, further comprising a set of at least three alternative contiguous semiconductor regions that are electrically isolated by a layer of material, the alternative set of regions having a different doping specificity, wherein the three alternative contiguous semiconductor regions are configured and arranged to operate in place of the first mentioned at least three contiguous semiconductor regions.

8. The apparatus of claim 1, further including beads on the surface of the sandwiched region and facing the fluidic channel, wherein the target materials attach or associate with the beads.

9. The apparatus of claim 1, wherein the sandwiched semiconductor region has a layer overlaying said semiconductor region so as to create a semiconductor sensor.

10. The apparatus of claim 9, wherein the surface of the semiconductor sensor exposed toward the fluidic channel is textured to increase sensitivity, and wherein the layer overlaying the semiconductor region is an insulator or metal.

11. The apparatus of claim 1, wherein the passing current is indicative of a conductance characteristic of the fluidic channel.

12. The apparatus of claim 1, further comprising a comb-like structure that connects the sandwiched region to the two of the other semiconductor regions.

13. The apparatus of claim 1, wherein the apparatus is one sensor in a high density sensor array.

14. The apparatus of claim 13, wherein the array comprises at least 100,000 sensors.

15. The apparatus of claim 1, wherein the at least three electrically-contiguous semiconductor regions are electrically coupled to the fluidic channel.

16. A method of using the apparatus of claim 1, comprising:
providing a fluid, including target materials, through the fluidic channel;
applying an electric field in and around the channel to facilitate sensitivity by inducing movement of molecules in the fluid;
applying a bias voltage to the sandwiched region; and
sensing the presence of the target materials by detecting current being passed in a conducting mode in response to the voltage resulting from the presence of the target materials.

17. The method of claim 16, wherein applying the electric field utilizes electrophoresis.

18. The method of claim 16, wherein applying the electric field utilizes electroosmosis.

19. The method of claim 16, wherein the step of sensing includes transitioning from a non-conducting mode to the conducting mode.

* * * * *